United States Patent [19]

Payton

[11] Patent Number: 4,593,688
[45] Date of Patent: Jun. 10, 1986

[54] APPARATUS FOR THE DELIVERY OF OXYGEN OR THE LIKE

[76] Inventor: Hugh W. Payton, 36 S. Main St., Jeffersonville, Ohio 43128

[21] Appl. No.: 615,195

[22] Filed: May 30, 1984

[51] Int. Cl.⁴ .......................................... A61M 10/00
[52] U.S. Cl. ........................... 128/200.28; 128/204.18; 128/205.24; 128/201.22
[58] Field of Search ............... 128/200.11, 200.14, 128/200.24, 200.28, 201.22, 201.23, 201.24, 203.12, 203.16, 203.17, 203.29, 204.11, 265.26, 207.13, 207.15, 201.28, 201.29, 205.25, 910, 201.15, 206.21, 206.28, 207.11; 2/DIG. 1

[56] References Cited

U.S. PATENT DOCUMENTS

| | | | |
|---|---|---|---|
| 2,391,565 | 12/1945 | Grindrod et al. | 128/205.28 |
| 2,469,273 | 5/1949 | Parker | 128/205.25 |
| 2,507,705 | 5/1950 | Gaddini | 128/205.25 |
| 2,525,236 | 10/1950 | Palmer | 128/205.25 |
| 2,617,415 | 11/1952 | Rosen et al. | 128/205.25 |
| 2,764,152 | 9/1956 | Osterberg | 128/201.23 |
| 3,112,745 | 12/1963 | Boyer | 128/201.23 |
| 3,441,020 | 4/1969 | Wortz et al. | 128/207.11 |
| 3,683,907 | 8/1972 | Cotabish | 128/200.28 |
| 3,955,570 | 5/1976 | Hutter | 128/910 |
| 4,055,173 | 10/1977 | Knab | 128/910 |
| 4,195,363 | 4/1980 | Jenson | 2/DIG. 1 |
| 4,233,972 | 11/1980 | Hauff et al. | 128/200.28 |
| 4,406,283 | 9/1983 | Bir | 128/207.18 |

FOREIGN PATENT DOCUMENTS

| | | | |
|---|---|---|---|
| 167663 | 5/1956 | Australia | 128/205.25 |
| 25187 | 1/1963 | German Democratic Rep. | 128/200.28 |
| 0003548 | 10/1982 | PCT Int'l Appl. | 128/207.13 |

*Primary Examiner*—Henry J. Recla
*Assistant Examiner*—Karin M. Reichle
*Attorney, Agent, or Firm*—Biebel, French & Nauman

[57] ABSTRACT

A system for applying a controlled atmosphere for breathing by a patient, in the treatment of croup or the like, includes a head piece which has a portion extending over the temple, a portion extending over the top of the head in the form of adjustable straps, and an elastic strap extending behind the head. A front support frame is connected to the head piece, and a U-shaped flexible gas delivery tube is supported on the frame. Nebulized oxygen enriched fog may be delivered from a nebulizer to the tube and emitted through orifices formed on an inside surface of the tube, at the ascending portions near the corners of the horizontal bottom portion, to form streams which are directed toward each other and which coalesce at a region in front of the face and mouth of the patient, for breathing by the patient. The support frame is pivotally mounted on the headgear so that it may be moved from its normal lowered position to a raised position to move the delivery tube out of the patient's way for eating and drinking.

6 Claims, 5 Drawing Figures

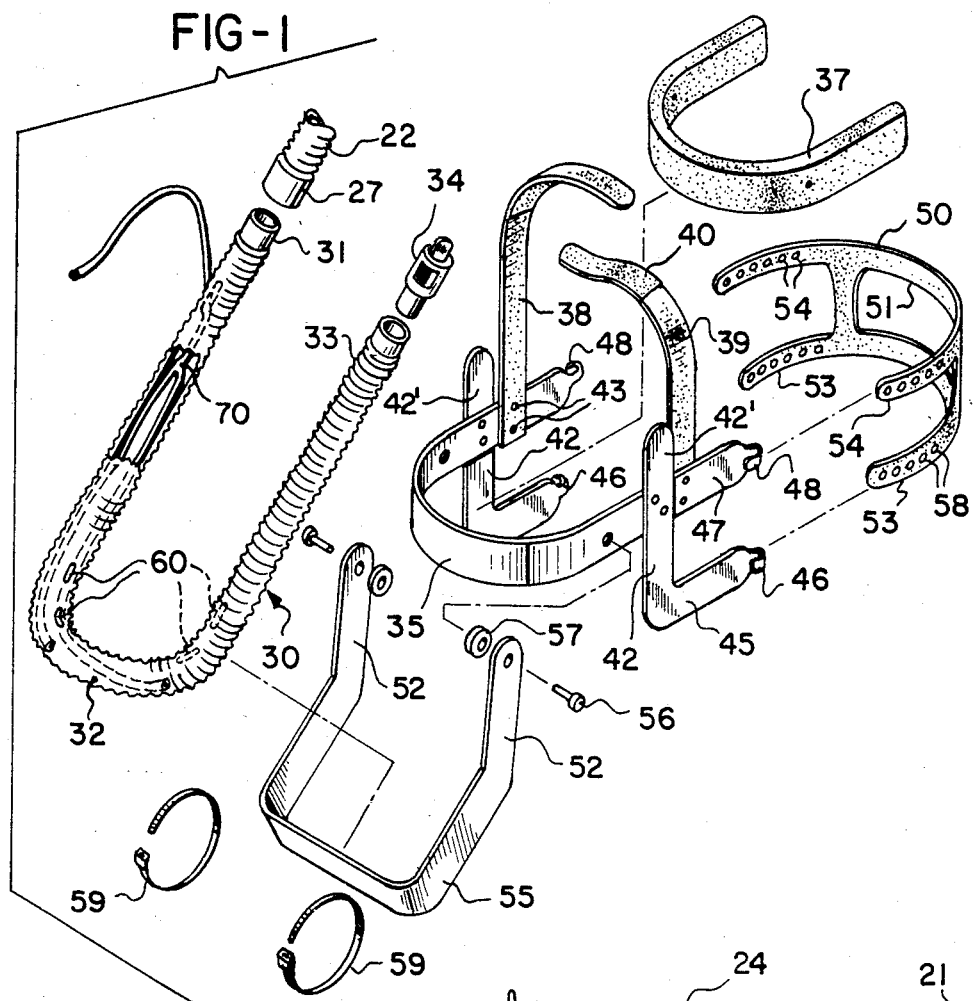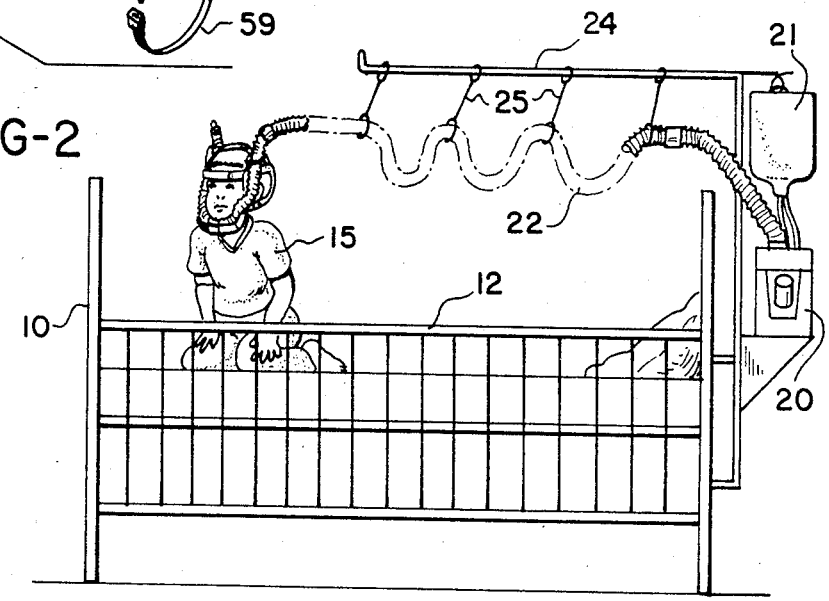

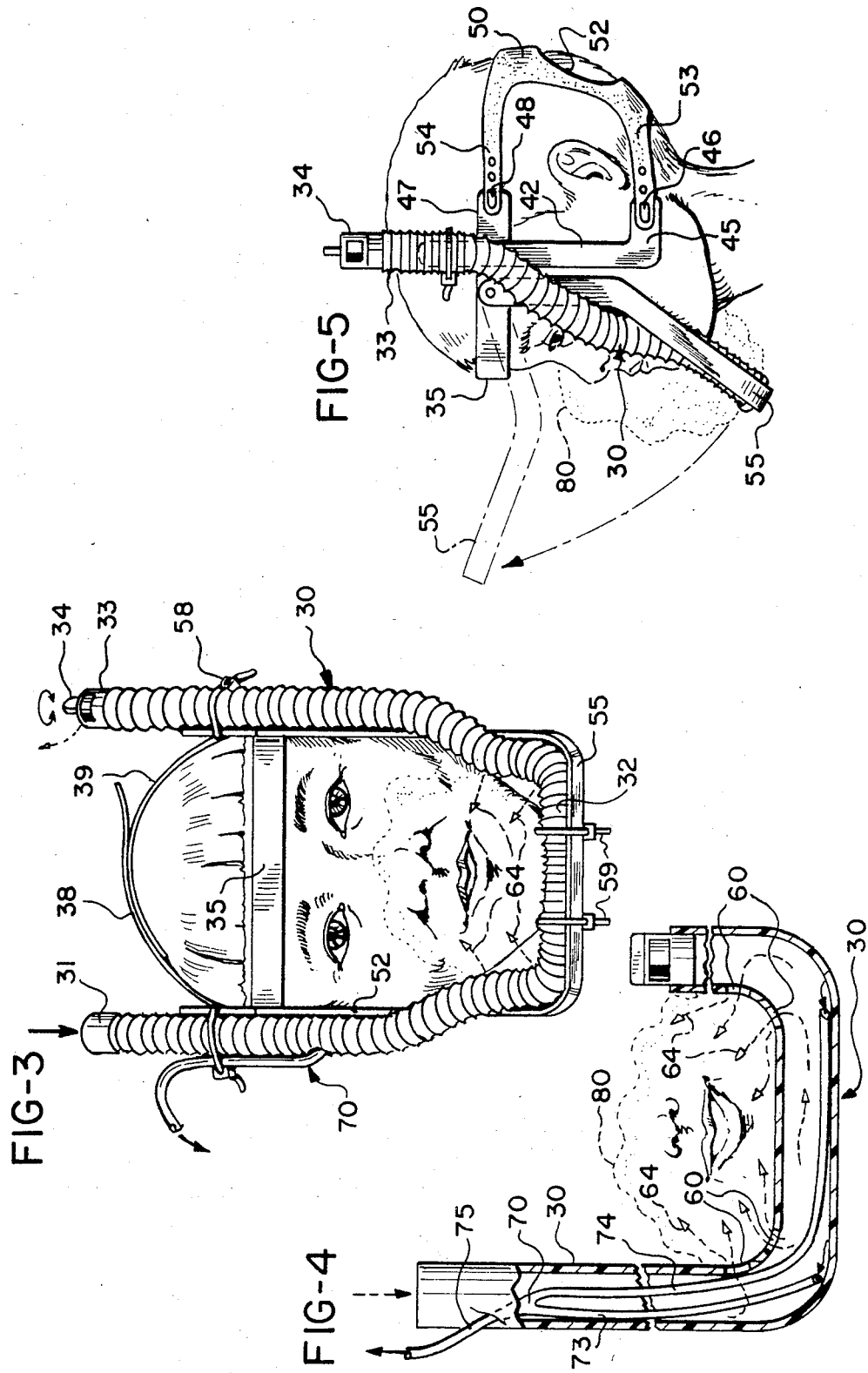

APPARATUS FOR THE DELIVERY OF OXYGEN OR THE LIKE

BACKGROUND OF THE INVENTION

This invention relates to apparatus for delivery of a controlled atmosphere to a patient requiring such atmosphere, and more particularly to apparatus which is capable of delivering oxygen, or nebulized water vapor or a combination of the same to a patient, such as a child, for the treatment of croup or the like. The apparatus of the present invention has further application in instances where it is not desirable or impossible for a patient to wear a conventional oxygen mask, such as where a patient has had facial injuries or has been involved in plastic surgery or reconstructive procedures, where it is otherwise not desirable to impossible for the patient to wear a conventional mask against his face.

It is well known to use humification of air to aid in respiratory health during winter months and in disease states affecting the upper and lower respiratory systems. Parents have resorted to steam emanating from showers, teakettles, vaporizers beneath umbrellas, etc., to treat croup, congested nasal passages, and severe coughing paroxysms. Medication, administered under hospital supervision, has subjected patients to cold mists, croup tents, moisture laden oxygen and the like, to provide relief of coughing, shortness of breath and to loosen bronchial mucus in passages.

In the treatment of croup, for example, it is currently the practice to by place an acutely ill, frightened patient, commonly a child, who may be laboring to breath, tired, and coughing, with or without temperature, into a croup tent. Advantages of use of such croup tent are very high humidity in a plastic enclosure with a temperature of plus or minus 60° F. Fog or mist in the tent is intentionally heavy and the outline of a patient can barely be delineated when placed in such a cold croup tent. Condensation within the tent trickles down the inner plastic walls of the tent, and the bedclothing and child's clothing become wet. The hair of the patient's head becomes soaked while 60° F. fog continues to emanate from the head piece of the tent bellows. Compounding the physical discomforts associated with such procedure, the patient, often a young child, is separated from its parents, creating more concern to the patient than his inability to breath.

In the proper operation of a croup tent, a tight fitting canopy must be maintained in order to prevent leakage and loss of oxygen and moisture. Small zippered openings in the canopies have been provided by which a parent can hold a child's hand to calm the child and reassure it. The proper operation of a croup tent requires that the child be covered by a dry blanket, but this is not always possible, particularly during the night. The proper operation also requires that the child's clothing be changed whenever it is damp to the touch, but again, this is often impractical and is not done. Whenever the child is removed from the tent, it is necessary to wipe excess moisture from the skin and hair and wrap the child in a dry blanket. Depending upon the severity of the affliction, a child may require the services of a croup tent for approximately three to five days, depending upon the reason for the therapy and the number of hours per day that the child is in the tent. Accordingly, not only does the tent provide a traumatic experience for the child, but the environmental conditions present within the tent require frequent monitoring.

SUMMARY OF THE INVENTION

The invention is directed to a wearable device through which a controlled atmosphere is presented to the region of the nose and mouth a patient, by defining a localized region of gases, for breathing. In the treatment of croup in children, the apparatus may be employed for the purpose of delivering nebulized moisture or water in the form of a fog, enriched with oxygen, at a cool temperature, for breathing by the child in a relatively open system. The apparatus of this invention may be used by both children and adults in other instances. Thus, the equipment could be used by a child or an adult at home as a low-priced system for delivering nebulized fog, even where oxygen was not present, but where humidification could be of advantage. Adult emphysema and bronchitis victims, for example, frequently require humidified air to assist in liquefying colds and secretions. Additionally, accident victims and patients having reconsructive surgery may require oxygen in situations where it is undesirable to place an oxygen mask in direct contact with the facial region of the patient.

A head supported apparatus is employed for supporting a delivery arrangement. In the treatment of croup, oxygen-rich moisture saturated vapor is received from a nebulizer as a fog under low pressure. The nebulizer may be one which is now used for the croup tent. The delivery system provides for the delivery of the vapor or fog to the patient, in an open system, by means of a plurality of streams which coalesce generally in front of the region of the nose and mouth, but not necessarily on the face itself, and not necessarily impinging upon the face. Thus, the invention provides apparatus by which a localized region is formed immediately in front of the face for breathing. Accordingly, in the case of a nebulizer, the front of the patient's face becomes moist while the rest of the patient remains dry.

The apparatus includes a comfortable support which, for the purpose of acceptance by a child, may simulate a space helmet, a football helmet or the like. The support takes the form of head-encircling adjustable straps which are comfortable to wear, and which may be worn while the patient is sitting up or lying down. A delivery tube is mounted on the head support. The delivery tube has a lower transverse portion which is positioned in front of the face or chin, and which is provided with openings or orifices from which streams of gases flow, such as from the nebulizer. The streams are directed in such a manner as to coalesce at a common zone or region in front of the patient's nose and mouth. The delivery tube arrangement may be provided with a valve by which the flow rate may be controlled.

In the case of a child, in order to provide for mobility, the delivery tube is connected to the nebulizer through an extended supply line which joins at one end to the delivery tube, and at another end to a nebulizer, which may be supported on the child's bed. The intermediate section of the supply line may be supported in an overhead sling-like arrangement, such as on curtain-hanging rings or the like, so that the same is free to move or slide, thus providing the child with some mobility and freedom of movement within the crib or bed.

In the preferred form of the apparatus, a flexible corrugated delivery tube is bent in a U-shape in front of the face of a patient and supported thereon by the headgear. It is provided near the bottom portion with orifices or openings of controlled size through which gas or fog from the nebulizer is directed into a generally common focal region forwardly of the nose and mouth. At this point, a plurality of such streams coalesce and form an atmosphere for breathing by the patient. The quantity of gas or fog so emitted may be accurately controlled, according to conditions.

The apparatus of this invention accordingly provides an arrangement by which the output of a nebulizer or the like may be accurately applied to a patient, in an open, generally non-contacting system, in which no parts of the apparatus come into direct contact with any of the facial regions. In addition, when the apparatus is used for the treatment of croup, it eliminates the necessity for a total tent enclosure, and this eliminates the disadvantage of having to subject a patient, such as a child, to such an environment.

A further object of the invention is the provision of apparatus for creating a localized region or zone of nebulized gas or fog immediately in front of the facial region of a patient.

A further object of the invention is the provision of headgear for supporting a water-saturated, oxygen-delivery system, from a nebulizer, for delivery to a patient, such as a child suffering from croup.

Another object of the invention is the provision of self-contained apparatus, supported by headgear, for applying a nebulized water and oxygen fog to a patient, without the necessity for fully enclosing the patient.

A still further object of the invention is the provision of apparatus, which is light in weight and readily portable, and adapted to use in a home or the like, and further adapted for the treatment or administration of oxygen to patients which, for whatever reason, cannot tolerate the application of a facial mask.

These and other objects and advantages of the invention will be apparent from the following description, the accompanying drawings and the appended claims.

BRIEF DESCRIPTION OF THE DRAWINGS

FIG. 1 is an exploded prospective view of apparatus according to my invention;

FIG. 2 is an elevational view showing a child wearing the apparatus in a crib;

FIG. 3 is a frontal view of the apparatus as applied to a child's head;

FIG. 4 is a fragmentary transverse sectional view of the delivery tube portion of the apparatus; and FIG. 5 is a side elevation of the apparatus as mounted on a child's head.

DESCRIPTION OF THE PREFERRED EMBODIMENT

Referring first to FIG. 2, a typical hospital crib bed 10 is shown with raisable side rails 12. A child 15 has been admitted for application of medication including a cool saturated fog of nebulized water and oxygen mixture. A nebulizer 20 is shown as mounted on one end wall of the crib 10 with a water supply 21, and having a connection to the hospital oxygen system (not shown). A nebulizer is designed to provide a source of aerosol or nebulized oxygen enriched air and water in the form of a cool fog under low pressure, through a flexible corrugated delivery hose 22.

The nebulizer itself may internally provide a film of liquid, such as water, for aersolization, by flowing the air over a hollow sphere. A small orifice in this sphere expels gas at supersonic velocity. This velocity ruptures the thin film of liquid and produces a continuous dispersion or fog of fine liquid particles, with the liquid particles being distributed in the range of 10 microns or less, and may have a mean diameter of 3 microns. A typical nebulizer may be model H-2101 sold under the trademark "Maxi-Cool" by the McGaw Respiratory Therapy Division of American Hospital Supply Corporation, Irvine, Calif. 92714.

An adequate length of the flexible delivery tube 22 is provided, with slidable hangers 25 which may suspend a major portion of the hose 22 from a rod 24, in the manner of a curtain rod, to provide for mobility of the patient in waking hours and permitting the patient, such as a young child, to move about the crib without undue restraints.

The flexible supply hose 22 delivers the fog to the applicator apparatus of this invention as shown in FIG. 1. The supply hose 22 terminates in a fitting 27, which telescopically interfits with flexible fog-administering delivery tube 30, which may be formed of the same material as that of the hose 22. The fog-administering tube 30 is formed in a generally U-shaped configuration with an inlet 31, a bottom portion 32, and an outlet 33. The inlet 31 is adapted to be releasably received in the fitting 27. An adjustable stopcock 34 is received in the outlet 33, by means of which the pressure within the tube 30 may be regulated, by suitably rotating the stopcock 34 and restricting the outflow of fog therefrom.

The tube 30 is supported and retained, on a headgear apparatus which includes an aluminum splint 35 curved to be received about the contour of the forehead and temples, and extending on each side of the head just above the ears, as shown in the side elevation in FIG. 5. The splint 35 may accordingly be considered as a forehead band, and may be lined with a pad 37 of soft conforming foam material, for comfort. A pair of head straps 38 and 39 extend upwardly from medium portion of the forehead band 35, such as from a position slightly in front of the ears perpendicularly to the axis of the forehead band 35, and are mutually overlapping at their ends, so as to be comfortably received over the head of the patient. The respective outer and inner surfaces of the terminal ends of the bands 38 and 39 may be provided with any suitable releasable fastening means 40, such as Velcro, so that adjustments may be made to head size and shape.

The forehead band 35 is further provided with a pair of L-shaped downwardly and rearwardly extending appendages 42. Each of the appendages 42 may be made of aluminum and suitably lined on their respective inside surfaces with foam padding for comfort. The upper arms of the appendages 42 are suitably secured, such as by rivets 43, to an outer side surface of the headband 35, just forwardly of the attachment of the straps 38 and 39, while the rearwardly extending portion 45 thereof is terminated in a hook 46. Similarly, the remaining rearwardly extending portions 47 of the headband 35 terminated at corresponding hooks 48.

Means for retaining the headgear in comfortable relation to the head of a patient, such as a child, includes a generally H-shaped elastic strap 50. The strap 50 may be of the general type now in common use for the retention of oxygen masks. For this purpose, the strap 50 is proportioned so that the center opening 51 receives the posterior prominence of the head, with the laterally extending strap portions 53 and 54 in overlapping relation, respectively, to the rearwardly extending portions 45 and 47, previously described. The forwardly extending strap portions 53 and 54 are provided with hook-receiving openings or apertures 58, which are adapted to be impaled over the hooks 46 or 48, for holding the elastic strap 50 and the headband 35 in a comfortable adjusted position.

The band 35 also pivotally supports the rearwardly and upwardly extending arms 52 of a generally U-shaped tube-supporting frame 55. The frame 55 actually has the appearance of a face guard, and the arms 52 are pivotally attached to the forehead band by means of rivets 56. Elastomer washers 57 may be interposed between the arms 52 and the band 35 to provide a frictional self-holding coupling for the frame 55 to the band 35.

The shape and size of the frame 55 conforms closely to the general outer contour of the delivery tube 30, at the lower end thereof, and provides means for supporting the delivery tube on the headgear, with the lower U-shaped portion 32 thereof received on the inwardly facing surface of the frame 55 and retained by a pair of plastic ties 59. The assembled relationship of the parts is best shown in FIGS. 3 and 4, where it is seen that the tube 30, at the lower end 32, is carried on an inside surface of the frame 55 whereas the outwardly extending arm portions of the tube 30 are conveniently carried adjacent the outer surface of upwardly extending segments 42' of the L-shaped appendages 42, for securing an attachment thereto by additional ties 59. The ends of the tube 30 are somewhat elevated above the patient's head for ease of attachment, correction or adjustment. The frame 55, as best shown in FIG. 5, may be moved between a lower operative position, and a raised position, in front of the head, in which the lower end 32 of the tube 30 is carried upwardly away from the patient's face to permit ease of eating, drinking, or the like.

The tube 30 is provided with means in the form of apertures or orifices 60, primarily at the bend joining in the ascending portions with the bottom-most portion 32, by means of which gas, such as nebulized fog, is forcefully propelled in intersecting cross streams, at a generally frontal region in front of the nose and the mouth of the patient, as shown in FIGS. 3 and 4. Preferably four such openings 60 are provided, two in each of the ascending limbs of the tube 30 just at the bend 62, on an inside surface, so that the streams 64 coalesce at a conglomerate region. It is preferred that the streams do not impact directly against the face of the wearer, but rather coalesce a short distance forward of the face, such as ½ to 1 inch. The amount of the gas or fog may be adjusted by suitably rotating the stopcock 34 at the end, again as best shown in FIGS. 3 and 4.

The orifices 60 may preferably be formed as small slits or openings formed directly into the side wall of the tubing. The openings are controlled as to size and position so that the streams emanating therefrom generally tend to coalesce together at a region immediately forward of the nose and mouth of a patient when the headgear is worn.

When used with a nebulizer, it can be expected that a certain amount of free liquid will tend to drain and accumulate into the lower portion 32 of the delivery tube 30. To prevent unwanted accumulation, a bifurcated suction tube 70 is preferably located within the tube 30 with depending legs 73 and 74 respectively located within the inside surface of the tube 30 at the bends. The main stem 75 of the tube 70 may then be extended through a side wall opening in the tube to a conventional suction apparatus. The distal ends of the legs 73 and 74 continually pick up accumulations of water, for removal from the tube. If desired, additional suction pickups may be placed at the lower portions of convolutions of the principal fog supply hose 22, leading from the nebulizer 20, for the purpose of extracting accumulations of moisture as desired or required.

It should be understood that the invention is not limited to the particular kind of headgear disclosed, although the preferred embodiment is both comfortable and stable with respect to the geometry of the head. The generally U-shaped nose guard or bracket 55, which supports the major weight of the delivery tube 30, is conveniently movable away from the face and mouth region, whenever desired, to permit eating and drinking. The headgear thus serves the primary object of supporting the delivery tube 30, in non-contacting relation to the face, with the exit orifices 60 properly positioned with respect to the facial features of the patient so that the converging streams 64 therefrom are most effectively or efficiently organized and positioned. Since the streams do not directly impinge upon the patient, only minimal wetting or moisturizing may occur in the facial regions. The remainder of the patient, including its clothing, and its surrounding bedding, have the optimum opportunity of remaining essentially dry and unaffected. The stream 64 emanating from the orifices 60 tend to coalesce and form an oxygen-enriched fog or region, illustrated by the broken lines 80 in FIGS. 4 and 5. It will be appreciated that the oxygen-enriched region 80 will not have a precise form or shape, but the broken lines are intended to represent a region of maximum concentration of fog, for breathing by the patient, immediately at and in front of the patient's nose and mouth.

The oxygen enriched cool fog, supplied by the nebulizer 20, will be most effectively used without the necessity of a totally enclosed environment such as a tent. The headgear and attending hose may be suitably decorated or dressed in such a manner as to appeal to a child and be accepted, and could accordingly be made to simulate a space helmet, a diver's helmet, or even a professional football helmet. The apparatus provides reasonably freedom of mobility for the child, during its period of confinement, and further permits the administration of the desired medication in a manner which permits the child to be otherwise unaffected by the cold vapors or wetness.

As has been noted above, the apparatus of the present invention is not intended to be limited for the treatment of croup in young patients, although this is one of the preferred uses of the apparatus. The apparatus is light in weight and accordingly readily portable and may be used in a home with home-type nebulizers for the application of moisture, without oxygen enrichment, to adult patients or children who may need a humidification from time to time. Further, the apparatus may be employed for the care of patients, requiring only oxygen, in instances where it is not practical or it is impossible to place an oxygen mask on the face, such as in the case of accident or burn victims or cases where the patient has undergone surgery in facial regions, or where it is otherwise impractical or impossible to use a mask.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. Apparatus adapted to be supported on the head of a patient for controllably supplying gas from a source of gas under low pressure to the mouth and nose region of the patient for breathing by the patient, comprising:

a head piece having lateral side members adapted to extend around the patient's head and transverse members connected to said lateral members and proportioned to extend transversely of the head over the top and along the sides of the head and means for joining said transverse members at the top of the patient's head, a frontal support frame having a generally U-shaped bottom and a pair of side arms connected to the free ends thereof, respectively, means for connecting said side arms to said head piece at said lateral side members thereof with said bottom of said support frame adapted to be received below the chin of the patient, a flexible gas delivery tube for delivery of gas from the source of gas to the patient having a remote open end adapted for connection to the source of gas and an open end opposite said remote end, means for supporting a portion of said gas delivery tube on said frontal support frame such that the tube extends continuously along said frame side arms and said bottom, thereby defining a descending section of said tube extending from said remote end along one of said side arms, a transverse section thereof extending along said bottom, and terminating in an ascending section thereof extending along the other side arm leading to said opposite open end, means for closing the opposite open end of said tube above said ascending section thereof, and orifice means formed in said tube at the transitions between said descending and ascending tube sections and said transverse tube section, said orifice means being positioned in said delivery tube to direct generally lateral intersecting streams of the gas therefrom at a common region generally forward of the nose and mouth of the patient and avoiding direct impingement of said streams against the nose and mouth to provide a coalescing gas region immediately forward of the nose and mouth of the patient for breathing by the patient.

2. The apparatus of claim 1 in which said tube closing means comprises valve means for controlling the pressure of the gas in said tube thereby controlling the rate of emission of the gas through said orifice means.

3. The apparatus of claim 2 in which said valve means comprises rotary stopcock means for emitting gas from said tube into the atmosphere.

4. The apparatus of claim 1 in which the source of gas adapted for connection to the apparatus is a nebulizer for applying a cool oxygen enriched fog to the patient for the treatment of croup.

5. The system of claim 1 in which said frontal support frame is pivotally mounted to said head piece for raising and lowering movement.

6. Apparatus adapted to be supported on the head of a patient for controllably supplying gas under relatively low pressure from a nebulizer to the mouth and nose region of a patient for breathing by the patient for the treatment of croup in children, comprising:

a head piece, said head piece having an upper band portion proportioned to extend over the top of the head of the patient with lateral opposite ends proportioned to extend down the sides of the head of the patient, a front band portion proportioned to extend across the forehead of the patient and having opposite lateral ends proportioned to extend along the sides of the patient's head, means for joining said frontal band portion with said upper band portion at the respective lateral ends thereof, and means for securing the band portions to the head of the patient, a frontal support frame having a generally U-shaped configuration including a bottom and a pair of side arms, means for pivotally connecting said support frame side arms to said head piece at the opposite ends of said frontal band portion with said bottom thereof adapted to be received below the chin of the patient and movable on said head piece between a normally lowered position in which said bottom is positioned below the chin and a raised position in which said support frame bottom is pivoted out of the way of the mouth region of the patient for eating and drinking, a flexible gas delivery tube for delivery of gas from said nebulizer to the patient having a remote open end adpated for connection to the nebulizer and an open end opposite said remote end, means for supporting a portion of said gas delivery tube generally continuously along the inside surfaces of said frontal support frame and along said frame side arms and said frame bottom thereby defining a descending section of said tube along one of said frame side arms leading from said remote end, a transverse section along said frame bottom and an ascending portion along the opposite frame side arm leading to said opposite open end, means for closing the opposite open end of said tube above said ascending section, and gas emitting orifices formed in said tube generally at the transition regions thereof between said ascending and descending tube sections and said transverse tube section, said orifices being positioned to direct a plurality of lateral and intersecting streams of gas from said tube generally into a common region directly in front of the nose and mouth of the patient while avoiding direct impingement thereof against the nose and mouth, to provide a coalescing gas region immediately forward of the nose and mouth for breathing by the patient.

* * * * *